United States Patent [19]

Russ et al.

[11] Patent Number: 5,484,458
[45] Date of Patent: Jan. 16, 1996

[54] TRIPHENDIOXAZINE COMPOUNDS, PROCESSES FOR THEIR PREPARATION AND THEIR USE AS DYESTUFFS

[75] Inventors: Werner H. Russ, Flörsheim; Horst Tappe, Dietzenbach; Christian Schumacher, Frankfurt am Main, all of Germany

[73] Assignee: Hoechst Aktiengesellschaft, Frankfurt, Germany

[21] Appl. No.: 243,111

[22] Filed: May 16, 1994

[30] Foreign Application Priority Data

May 18, 1993 [DE] Germany .......................... 43 16 539.7
Feb. 2, 1994 [DE] Germany .......................... 44 03 065.7

[51] Int. Cl.$^6$ ...................... C09B 62/002; C09B 62/503; C09B 67/22; D06P 1/38
[52] U.S. Cl. .......................... 8/549; 8/638; 8/639; 8/643; 8/917; 8/918; 8/924; 544/76
[58] Field of Search .................. 544/76; 8/549, 8/917, 918, 924, 638, 639, 641, 643

[56] References Cited

U.S. PATENT DOCUMENTS

| | | | |
|---|---|---|---|
| 5,085,668 | 2/1992 | Pelster et al. | 8/549 |
| 5,122,605 | 6/1992 | Pedrazzi | 544/76 |
| 5,139,533 | 8/1992 | Hildebrand | 8/502 |

FOREIGN PATENT DOCUMENTS

| | | | |
|---|---|---|---|
| 0568860 | of 0000 | European Pat. Off. | C09B 62/04 |
| 0499588A1 | 2/1992 | European Pat. Off. | |

0568860A1  4/1993  European Pat. Off. .

*Primary Examiner*—Margaret Einsmann
*Attorney, Agent, or Firm*—Connolly & Hutz

[57] ABSTRACT

Triphendioxazine compounds corresponding to the formula

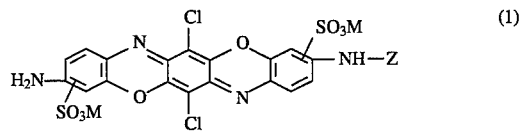
(1)

which are suitable as fiber-reactive dyestuffs for dyeing and printing material, in particular fiber material, containing hydroxy and/or carboxamide groups, such as wool and synthetic polyamide fibers, and especially cellulose fibers, such as cotton, are described. In formula (1), M is hydrogen or an alkali metal and Z is a radical of the formula (2)

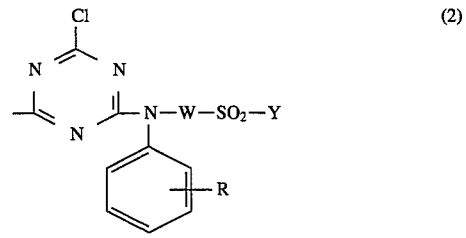

(2)

in which R is hydrogen, sulfo, alkyl having 1 to 4 carbon atoms, alkoxy having 1 to 4 carbon atoms, nitro or cyano, W is alkylene having 3 to 6 carbon atoms and the group —SO$_2$—Y is a fiber-reactive group of the vinyl sulfone series.

11 Claims, No Drawings

TRIPHENDIOXAZINE COMPOUNDS, PROCESSES FOR THEIR PREPARATION AND THEIR USE AS DYESTUFFS

FIELD OF THE INVENTION

The invention relates to the technical field of fiber-reactive dyestuffs.

DESCRIPTION OF THE PRIOR ART

Asymmetrically built-up fiber-reactive triphendioxazine dyestuffs, i.e. triphendioxazine dyestuffs in which one terminal benzene nucleus is substituted with amino group and the other terminal benzene nucleus contains a 2-halogeno-4-[N-phenyl-N-β-(β-sulfatoethylsulfonyl)-ethyl]-amino-1,3,5-triazin-6-yl-amino group or dichlorotriazinylamino-disulfophenylamino-chlorotriazinylamino group, are described in European Patent Application Publication No. 0 568 860 and British Patent No. 1 349 513.

SUMMARY OF THE INVENTION

By the present invention, novel triphendioxazine compounds corresponding to the formula (1)

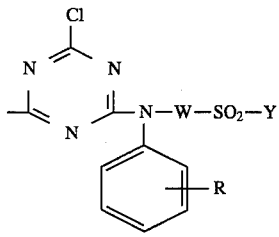

(1)

have been found, in which:

M is hydrogen or an alkali metal, such as sodium, potassium or lithium;

Z is a radical of the formula (2)

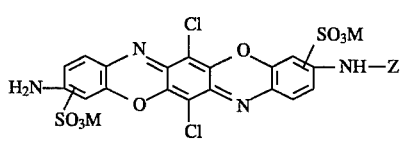

(2)

in which

R is hydrogen, sulfo, alkyl having 1 to 4 carbon atoms, such as ethyl and, in particular, methyl, alkoxy having 1 to 4 carbon atoms, such as ethoxy and, in particular, methoxy, nitro or cyano, W is alkylene having 3 to 6 carbon atoms, preferably isopropylene and, in particular, n-propylene, and Y is vinyl, or is ethyl which is substituted in the β-position by a substituent which can be eliminated under the action of alkali to form the vinyl group; and the two sulfo groups —SO$_3$M are preferably bonded in the ortho-position relative to the oxygen atom of the heterocyclic ring on the benzene nucleus.

Substituents in the ethyl group Y in the β-position are, for example, sulfato, thiosulfato, phosphato, alkanoyloxy having 2 to 5 carbon atoms, such as acetyloxy, benzoyloxy, sulfobenzoyloxy, p-toluenesulfonyloxy or halogen, such as bromine or chlorine. Y is preferably vinyl, β-chloroethyl and, in particular, β-sulfatoethyl. R furthermore is preferably hydrogen or sulfo, and particularly preferably hydrogen.

In addition to the particularly preferred 1,3-propylene, radicals W are, for example, 2-methyl-1,2-ethylene, 1-methyl-1,2-ethylene, 2-methyl-1,3-propylene, 1,4-butylene, 1,5-pentylene and 1,6-hexylene.

Triphendioxazine compounds of the formula (1) according to the invention which can be singled out in particular are those which correspond to the formula (1A)

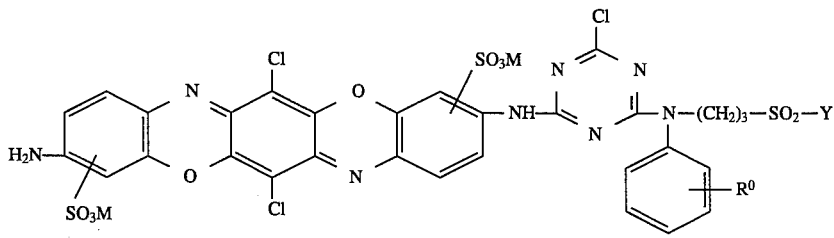

(1A)

in which M and Y have the abovementioned particularly preferred meanings and R$_0$ is hydrogen or sulfo.

In the formulae (1) and (2) and in the formulae below, the individual formula members both of different designations and of the same designation within a formula can have meanings which are identical to one another or different from one another within the context of their meaning.

The "sulfo", "carboxy", "phosphato", "thiosulfato" and "sulfato" groups include both the acid form thereof and the salt form thereof. Accordingly, sulfo groups are groups corresponding to the formula —SO$_3$M, carboxy groups are groups corresponding to the formula —COOM, phosphato groups are groups corresponding to the formula —OPO$_3$M$_2$, thiosulfato groups are groups corresponding to the formula —S—SO$_3$M and sulfato groups are groups corresponding to the formula —OSO$_3$M, in which M has the abovementioned meaning.

The present invention furthermore relates to a process for the preparation of the triphendioxazine compounds of the formula (1) according to the invention, which comprises reacting an amino substituted dichlorotriazinylaminotriphendioxazine compound of the formula (3)

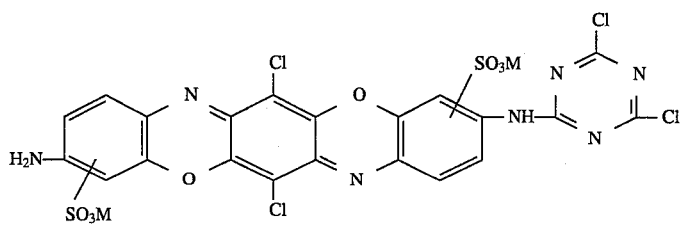
(3)

where M has the abovementioned meaning, with an amino compound of the formula (4)

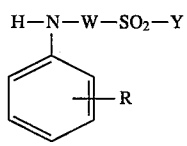

in which R, W and Y have the abovementioned meanings, in an aqueous or aqueous-organic medium at a pH of between 3 and 9, preferably between 4 and 5, and at a temperature of between 25° and 100° C., preferably between 40° and 80° C.

If the reaction is carried out in an aqueous-organic medium, the organic medium is a dipolar aprotic solvent which is inert towards the reactants and soluble in water or water-miscible, such as, for example, acetone, dimethylformamide, dimethylacetamide, sulfolane or N-methyl-pyrrolidone. Hydrochloric acid liberated during the condensation reaction is advantageously neutralized continuously by addition of aqueous alkali metal or alkaline earth metal hydroxides, carbonates or bicarbonates.

The preparation of the starting compound of the formula (3) is known per se (cf. European Patent Application Publication No. 0 448 815, Example 1, European Patent Application Publication No. 0 142 777, Example 44, and German Auslegeschrift No. 2 124 080, Example 1). The reaction between the diamino-triphendioxazine compound and the cyanuric chloride may thus be carried out at a pH of between about 4 and 7 and at a temperature of between about 0° and 25° C.

The starting compounds of the formula (4) have not yet been described to date. They can be prepared, for example, by reacting N-allyl-N-acetyl-aniline (cf. J. Org Chem. 14, 1099 (1949)), by a procedure analogous to that described in German Offenlegungsschrift No. 41 06 106, with 2-mercapto-ethanol in the presence of a free radical initiator, and oxidizing the resulting N-[γ-(β'-hydroxyethylthio)-propyl]-N-acetyl-aniline compound to the sulfonyl compound, for example by means of hydrogen peroxide in the presence of a catalytic amount of a transition metal compound, such as, for example, tungsten oxide. The acetyl group is split off hydrolytically from the resulting sulfonyl compound in the alkaline or acid range, preferably in hydrochloric acid aqueous solution, such as, for example, in 5 to 30% strength aqueous hydrochloric acid, at a temperature of between 80° and 100° C.

The N-phenyl-N-[γ-(β'-hydroxyethylsulfonyl)-propyl]-amine thus obtained can be separated off from the aqueous phase of the aqueous synthesis solution which has been rendered neutral. The β-hydroxyethylsulfonyl group thereof can be esterified by customary methods, i.e., for example, it can be converted into the β-sulfatoethylsulfonyl compound by means of concentrated sulfuric acid at a temperature of between 10° and 30° C., or into the β-chloroethylsulfonyl compound using thionyl chloride or gaseous hydrogen chloride.

Starting compounds of the formula (4) are, for example, N-phenyl-N- [β-(γ'-chloroethylsulfonyl)-propyl]-amine, N-(4-chlorophenyl)-N-[γ-(β'-chloroethylsulfonyl)-propyl]-amine, N-(2-methylphenyl)-N-[γ(β'-chloroethylsulfonyl)-propyl]-amine, N-(4-methoxyphenyl)-N-[γ(β'-chloroethylsulfonyl)-propyl]-amine, N-(3-sulfophenyl)-N-[γ-(β'-chloroethylsulfonyl)-propyl]-amine, N-(4-sulfophenyl)-N-[γ-(β'-chloroethylsulfonyl)-propyl]-amine, N-phenyl-N-(γ-vinylsulfonyl-propyl)-amine, N-(4-chlorophenyl)-N-(γ-vinylsulfonyl-propyl)-amine, N-(2-methylphenyl)-N-(γ-vinylsulfonyl-propyl)-amine, N-(4-methoxyphenyl)-N-(γ-vinylsulfonyl-propyl)-amine, N-(3-sulfophenyl)-N-(γ-vinylsulfonyl-propyl)-amine, N-(4-sulfophenyl)-N-(γ-vinylsulfonyl-propyl)-amine, N-phenyl-N-[γ-(β'-sulfatoethylsulfonyl)-propyl]-amine, N-(4-chlorophenyl)-N-[γ-(β'-sulfatoethylsulfonyl)-propyl]-amine, N-(2-methylphenyl)-N-[γ-(β'-sulfatoethylsulfonyl)-propyl]-amine, N-(4-methoxyphenyl)-N-(γ(β'-sulfatoethylsulfonyl)-propyl]-amine, N-(3-sulfophenyl)-N-[γ-(β'-sulfatoethylsulfonyl)-propyl]-amine, N-(4-sulfophenyl)-N-[γ-(β'-sulfatoethylsulfonyl)-propyl]-amine, N-phenyl-N-[β-methyl-γ-(β'-chloroethylsulfonyl)-propyl]-amine, N-phenyl-N-[β-ethyl-γ-(β'-chloroethylsulfonyl)-propyl]-amine, N-phenyl-N-[δ-(β'-chloroethylsulfonyl)-butyl]-amine, N-phenyl-N-[ε-(β'-chloroethylsulfonyl)-pentyl]amine, and N-phenyl-N-[β-(β-chloroethylsulfonyl)-hexyl]-amine, and of these particularly preferably N-phenyl-[γ-(β'-chloroethylsulfonyl)-propyl]amine, and N-phenyl-[γ-(β'-sulfatoethylsulfonyl)-propyl] amine.

The present invention furthermore relates to mixtures of one or more triphendioxazine compounds of the formula (1) with one or more other blue-dyeing compounds (dyestuffs), of a structure known per se, from the disazo, copper formazan, triphendioxazine and anthraquinone series. Such dyestuffs are, for example, triphendioxazine dyestuffs corresponding to the formula (I)

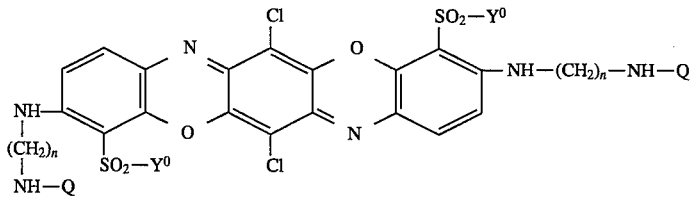

which are described, for example, in European Patent Application Publication Nos. 0 101 665, 0 153 599 and 58 493, anthraquinone dyestuffs corresponding to the formula (II)

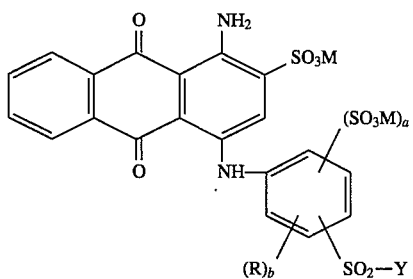

which are known from German Patent No. 965 902, copper formazan dyestuffs corresponding to the formula (III)

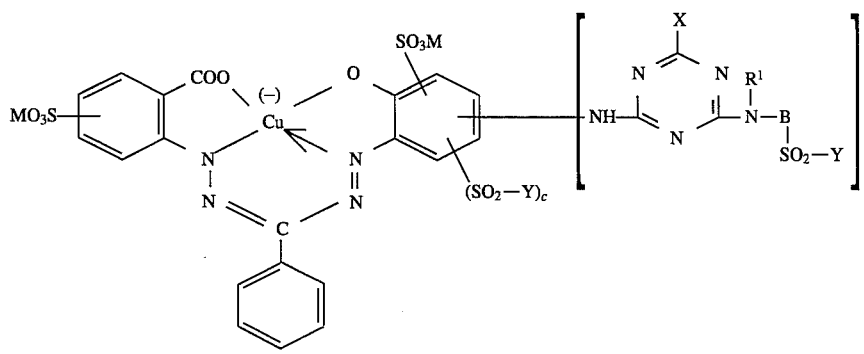

which are known, for example, from European Patent Application Publication Nos. 0 028 788 and 0 568 860, and disazo dyestuffs corresponding to the formula (IV)

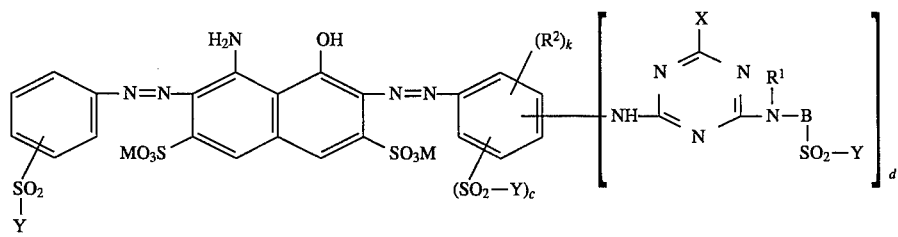

which are known, for example, from European Patent Application Publication No. 0 568 860 and from German Patent No. 965 902.

In the formulae (I) to (IV):

M and Y have one of the abovementioned meanings;

n is a number from 2 to 6;

$Y^0$ is hydroxy, vinyl, β-haloethyl, such as chloroethyl, or β-sulfatoethyl, preferably hydroxy or β-sulfatoethyl;

Q is hydroxy, sulfato, arylamino, alkylamino having an alkyl radical of 1 to 4 carbon atoms, dialkylamino having alkyl radicals of in each case 1 to 4 carbon atoms, alkylcarbonylamino having 3 to 7 carbon atoms, such as β-carboxypropionylamino, 4-chloro-6-arylamino-1,3,5-triazin-2-yl-amino, 4-fluoro-6-arylamino-1,3,5-triazin-2-yl-amino or 4-cyanoamino-6-arylamino-1,3,5-triazin-2-yl-amino, where the aryl radical in these radicals is a benzene or naphthalene radical which can be substituted by 1, 2 or 3 substituents from the group comprising sulfo, hydroxy, alkyl having 1 to 4 carbon atoms, such as ethyl and methyl, alkoxy having 1 to 4 carbon atoms, such as ethoxy and methoxy, β-sulfatoethylsulfonyl, β-haloethylsulfonyl, such as β-chloroethylsulfonyl, or vinylsulfonyl, where, in the case where Y is hydroxy, Q is one of the triazinylamino radicals mentioned, and in the case where Y is vinyl, β-haloethyl or β-sulfatoethyl, the radical Q is one of the abovementioned radicals having at least one sulfo group;

R is alkyl having 1 to 4 carbon atoms, such as, in particular, methyl;

a is the number zero, 1 or 2 (where, in the case where a is zero, this group is hydrogen);

b is the number zero, 1 or 2 (where, in the case where a is zero, this group is hydrogen);

c is the number zero or 1 (where, in the case where c is zero, this group is hydrogen) and d is the number zero or 1 (where, in the case where c is zero, this group is hydrogen), where the sum of (c+d) is 1;

X is chlorine or fluorine;

k is the number 1 or 2;

$R^1$ is hydrogen, phenyl, which can be substituted, such as, for example, by sulfo, alkyl having 1 to 4 carbon atoms, alkoxy having 1 to 4 carbon atoms or carboxyl, or is alkyl having 1 to 4 carbon atoms, such as ethyl and, in particular, methyl;

$R^2$ is hydrogen, sulfo, alkoxy having 1 to 4 carbon atoms, such as ethoxy and, in particular, methoxy, or alkyl having 1 to 4 carbon atoms, such as ethyl or, in particular, methyl, where, in the case where k is 2, the two substituents R can have different meanings; and B is an aliphatic or aromatic bridge member, such as, for example, alkylene having 1 to 6 carbon atoms and phenylene, which can be substituted, such as, for example, by 1 or 2 substituents from the group comprising sulfo, methyl, ethyl, methoxy, ethoxy, carboxy and nitro, or is a combination of an aliphatic and aromatic bridge member.

In the formula (I), in the case where Y is β-sulfatoethyl, the radical Q is preferably sulfato or β-carboxypropionylamino, and in the case where Y is hydroxy, the radical Q is preferably 4-fluoro-6-(2',5'-disulfophenyl)-amino-1,3,5-triazin-2-yl-amino.

These mixtures according to the invention as a rule comprise the compound or compounds of the formula (1) in an amount of 98 to 30% by weight, preferably 96 to 55% by weight, and the compound or compounds corresponding to the formulae (I), (II), (III) and/or (IV) in an amount of 2 to 70% by weight, preferably 4 to 45% by weight.

The mixture according to the invention of the compounds of the formula (1) with one or more compounds of the formulae (I) to (IV) can usually be prepared by mechanical mixing of the individual components. However, the compounds of the formulae (I) to (IV) can also be added in the corresponding amounts to the aqueous synthesis solution of the triphendioxazine compounds of the formula (I) according to the invention; they can thus be used for dyeing in the form of this aqueous solution, if appropriate after concentration or dilution with water and if appropriate after addition of a buffer substance. The addition of blue dyestuffs of the formulae (I) to (IV) has the advantage that the reddish-blue dyeings obtainable with the triphendioxazine dyestuffs of the formula (1) according to the invention can easily be adjusted in shade in the desired manner.

The compounds of the formula (1) prepared according to the invention can be separated out from the synthesis batches by generally known methods, either by precipitation from the reaction medium by means of electrolytes, such as, for example, sodium chloride or potassium chloride, or by evaporation of the reaction solution, for example by spray drying, it being possible for a buffer substance to be added to this reaction solution.

The compounds of the formula (1) and the mixtures according to the invention, which are described above, of one or more of the triphendioxazine dyestuffs of the formula (1) with one or more of the known dyestuffs of the formulae (I) to (IV)—both Generally called dyestuffs (1) below—are suitable for dyeing and printing the most diverse materials, such as silk, leather, wool, polyamide fibers and polyurethanes, and in particular all types of cellulose-containing fiber materials. Such fiber materials are, for example, the naturally occurring cellulose fibers, such as cotton, linen and hemp, as well as cellulose (pulp) and regenerated cellulose. The dyestuffs (1) are also suitable for dyeing and printing fibers containing hydroxy groups and contained in blend fabrics, for example mixtures of cotton with polyester fibers or polyamide fibers.

The dyestuffs (1) can be applied to the fiber material and fixed on the fiber in various ways, in particular in the form of aqueous dyestuff solutions and printing pastes. They are suitable both for the generally known exhaustion processes in wide temperature ranges, in particular at 60° to 80° C., and also for dyeing by the pad-dyeing process, in which the goods are impregnated with aqueous dyestuff solutions, which contain salts if appropriate, and, after treatment with an alkali or in the presence of alkali, the dyestuff is fixed, if appropriate under the action of heat. The dyestuffs (1) are preferably employed in the exhaustion processes. High-quality dyeings are then obtained in these processes even if the dyebath comprises only a small amount of one or more electrolyte salts, such as sodium chloride, potassium chloride and sodium sulfate, for example 20 to 40 g/l of dye liquor, in contrast to the amounts of 50 to 80 g/l generally used in the art. After fixing, the dyeings or prints are rinsed thoroughly with cold and hot water, if appropriate with addition of an agent which has a dispersing action and promotes diffusion of the non-fixed portions. These dyeing and printing processes are described in numerous instances in the general technical literature and also in the patent literature, such as, for example, in the publications mentioned at the beginning.

The present invention therefore also relates to the use of the dyestuffs (1) for dyeing (including printing) these materials and to processes for dyeing (and printing) such materials by a procedure customary per se, in which a dyestuff (1) is employed as the coloring agent, by applying the dyestuff (1) to the material in an aqueous medium and fixing it on the material by means of heat or by means of a compound having an alkaline action or by means of both.

The dyestuffs (1) are distinguished by a high reactivity, a good fixing capacity and a very good build-up capacity. The degrees of fixing are high, and non-fixed portions can easily be washed out, the difference between the degree of exhaustion and the degree of fixing being remarkably small, i.e. the soaping loss being very low. The dyestuffs (1) are also suitable for printing, above all on cotton, but also for printing nitrogen-containing fibers, for example wool or silk, or blend fabrics which contain wool or silk.

The dyeings and prints produced with the dyestuffs (1), especially on cellulose fiber materials, have a high color depth and a high fiber-dyestuff bond stability both in the acid and in the alkaline range, and furthermore a good light-fastness and very good wet-fastness properties, such as fastnesses to washing, water, seawater, crossdyeing and perspiration, as well as a good fastness to pleating, fastness to ironing and fastness to rubbing.

The following Examples serve to illustrate the invention. The parts are parts by weight and the percentage data are percentages by weight, unless noted otherwise. Parts by weight bear the same relation to parts by volume as the kilogram to the liter.

The compounds described by way of formulae in the examples are shown in the form of the free acid; in general, they are prepared and isolated in the form of their alkali metal salts, such as lithium, sodium or potassium salts, and are used for dyeing in the form of their salts. The starting compounds and components mentioned in the following Examples, in particular the Tabular Examples, in the form of the free acid can likewise be employed in the synthesis as such or in the form of their salts, preferably alkali metal salts.

The absorption maxima ($\lambda_{max}$) in the visible range stated for the dyestuffs according to the invention were determined with the aid of their alkali metal salts in aqueous solution. In the Tabular Examples, the $\lambda_{max}$ values are given in parentheses alongside the color shade; the wavelength data are in nm.

Example 1

A suspension of 30 parts of cyanuric chloride in 200 parts of ice-water is added to a solution of the lithium salt of 58.9 parts of 2,9-diamino-9,13-dichloro-1,8-disulfo-triphendioxazine in 1500 parts of water at 15 to 20° C., while maintaining a pH of between 6 and 7 by means of a lithium hydroxide solution. The mixture is subsequently stirred for a further short period of time and 52 parts of N-phenyl-N-δ-(β'-sulfatoethylsulfonyl)propylamine are then added as a solution in 100 parts of water. The mixture is heated to 50° to 60° C. and subsequently stirred again for some time, while maintaining a pH of between 4 and 5, and, when the reaction has ended, the triphendioxazine compound according to the invention is isolated in the customary manner, for example as the alkali metal salt (sodium salt) by salting out with sodium chloride. It has, written in the form of the free acid, the formula

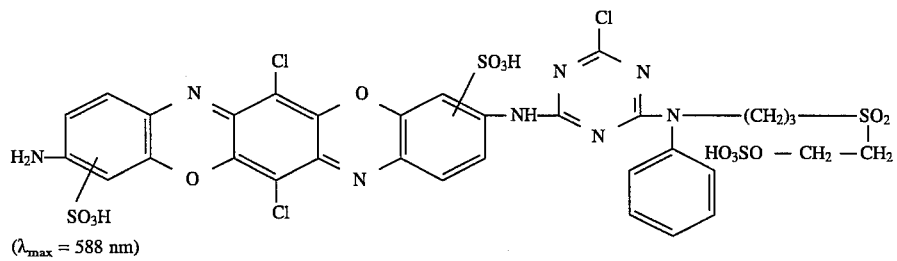

($\lambda_{max}$ = 588 nm)

and shows very good dyestuff properties. By the application and fixing processes customary in the art for fiber-reactive dyestuffs, it produces very deep, brilliant, reddish-blue dyeings and prints with a high fixing rate on the fiber materials mentioned in the description, in particular cellulose fiber materials, such as cotton.

Example 2

The synthesis of the triphendioxazine compound prepared in Example 1 can also be carried out by first reacting the starting diaminotriphendioxazine compound with cyanuric chloride in accordance with Example 1 and isolating the resulting dichlorotriazinylaminotriphendioxazine compound by salting out with sodium chloride. The moist filter cake is then dissolved in 500 parts of water; a solution of 33 parts of N-phenyl-N-γ-(β' -sulfatoethylsulfonyl)-propylamine in 100 parts of water is stirred into this solution. The batch is heated to 50° to 60° C. and subsequently stirred again for some time, while maintaining a pH of between 4 and 5. The triphendioxazine compound according to the invention is isolated in the customary manner. It has the same good properties as the triphendioxazine compound prepared as described in Example 1.

Example 3

The triphendioxazine compound according to the invention of Example 1 can be converted into the vinylsulfonyl derivative thereof by, for example, dissolving 100 parts of the triphendioxazine compound according to the invention of Example 1 in 1000 parts of water and adding sodium hydroxide solution at 25° C. until the mixture has achieved a pH of 12. The mixture is subsequently stirred for a further 30 minutes, while maintaining this pH and the stated temperature, and the compound according to the invention of the formula (written in the form of the free acid)

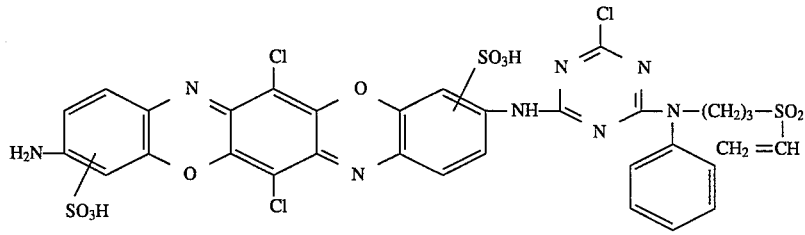

($\lambda_{max}$ = 584 nm)

is then isolated by salting out with sodium chloride. It likewise has very Good fiber-reactive dyestuff properties and gives, like the compound according to the invention of Example 1, deep, brilliant, reddish-blue dyeings and prints in high fixing rates on, for example, cellulose fibers.

Examples 4 to 8

Further triphendioxazine compounds according to the invention corresponding to the formula (A)

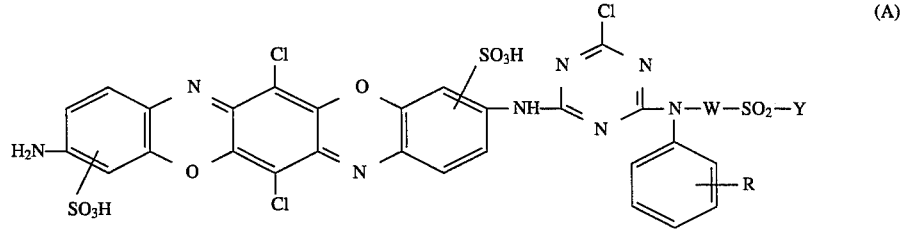

are described in the following Tabular Examples with the aid of the components which can be seen therefrom. They can be prepared in the manner according to the invention, for example analogously to the above Examples, by reaction of the starting compounds which can be seen from the formula radicals of formula (A). They have very good fiber-reactive dyestuff properties and give deep dyeings and prints, with the color shade stated for cotton in the particular Tabular Examples, on the fiber materials mentioned in the description, such as, in particular, cotton, by the application and fixing processes customary for fiber-reactive dyestuffs.

| Example | Triphendioxazine compound (A) | | | Color shade |
| --- | --- | --- | --- | --- |
| | Radical R | Radical W | Radical Y | |
| 4 | Hydrogen | 2-methyl-1,2-ethylene | β-sulfatoethyl | reddish-tinged blue (585) |
| 5 | 3-sulfo | 1,3-propylene | β-sulfatoethyl | reddish-tinged blue (582) |
| 6 | 4-sulfo | 1,3-propylene | β-sulfatoethyl | reddish-tinged blue (586) |
| 7 | 3-methyl | 1,3-propylene | β-sulfatoethyl | reddish-tinged blue (583) |
| 8 | 4-methoxy | 1,3-propylene | β-sulfatoethyl | reddish-tinged blue (584) |

Example A 100 parts of a cotton fabric are dyed by an exhaustion dyeing process in a customary dyeing apparatus with good liquor penetration as follows:

100 parts of a cotton fabric are added to a solution, warmed to 25° C. and contained in the dyeing apparatus, of part of the triphendioxazine dyestuff according to the invention of Example 1 and 30 parts of sodium chloride in 1000 parts of water with a pH of 6 to 7, and is first agitated in this dye liquor for 10 minutes. The temperature of the dye liquor is then increased to 80° C. in the course of 30 minutes, 2 parts of sodium carbonate are added and dyeing is continued at 80° C for a further 20 minutes. Thereafter, a further 3 parts of sodium carbonate are added, dyeing is continued at 80° C. for 20 minutes, a further 5 parts of sodium carbonate are added, dyeing is again carried out at 80° C. for 20 minutes and the dyed fabric is then removed from the dye liquor. It is finished in the customary manner by rinsing with cold and hot water, by treatment at the boil in a bath containing a nonionic detergent, by renewed rinsing with hot and cold water and by drying. A very deep, reddish-blue dyeing having a high degree of fixing is obtained.

Example B 0.6 part of the triphendioxazine dye according to the invention of Example 1 and 0.4 part of the triphendioxazine dye, known from European Patent No. 0 153 599, of the formula

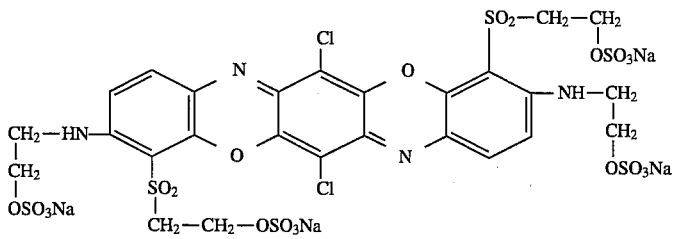

are dissolved together, either as a mixture or individually, in 1000 parts of water. 30 parts of sodium chloride are added to this dyestuff solution and a cotton fabric is dyed as described in Example A.

A very deep, blue dyeing, which is a shade more greenish than the dyeing obtainable according to Example A using the triphendioxazine dyestuff according to the invention, is obtained.

We claim:

1. A triphendioxazine compound of the formula (1)

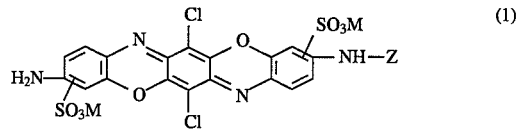

in which:

M is hydrogen or an alkali metal; and

Z is a radical of the formula (2)

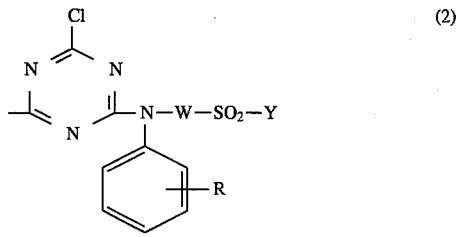

in which

R is hydrogen, sulfo, alkyl having 1 to 4 carbon atoms, alkoxy having 1 to 4 carbon atoms, nitro or cyano, W is alkylene having 3 to 6 carbon atoms and Y is vinyl, or is ethyl which is substituted in the β-position by a substituent which can be eliminated under the action of alkali to form the vinyl group.

2. A compound as claimed in claim 1, in which R is hydrogen or sulfo.

3. A compound as claimed in claim 1, in which W is 1,3-propylene or 2-methyl-1,2-ethylene.

4. A compound as claimed in claim 1, in which Y is vinyl, β-chloroethyl or β-sulfatoethyl.

5. A compound as claimed in claim 1, in which Y is β-sulfatoethyl.

6. A compound as claimed in claim 1 of the formula

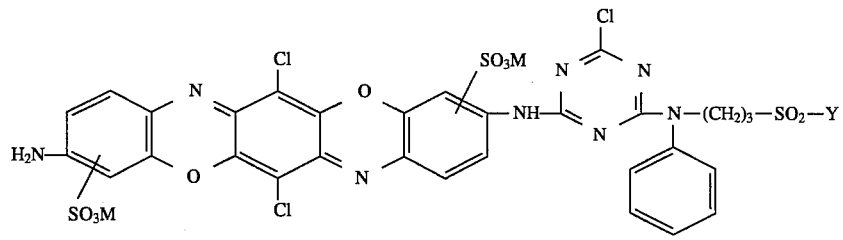

in which M and Y have the meanings given in claim 1.

7. A compound as claimed in claim 6, in which Y is β-sulfatoethyl.

8. A composition comprising a mixture of one or more triphendioxazine compounds of the formula (1) of claim 1 with one or more blue-dyeing compounds of different structure selected from the group consisting of disazo, copper formazan, triphendioxazine, and anthraquinone compounds.

9. A process for dyeing material containing hydroxy groups, carboxamide groups, or mixtures thereof, comprising the steps of bringing at least one dyestuff which is a compound as claimed in claim 1 into contact with the material in an aqueous dyebath comprising 20 to 40 g/l of electrolyte salt, and fixing the dyestuff or dyestuffs on the material by heating or adding an agent having an alkaline action, or by a combination of heat and addition of an agent having an alkaline action.

10. The process as claimed in claim 9, wherein the process for dyeing is an exhaustion dyeing process.

11. A process for dyeing material as claimed in claim 9, wherein the dyebath additionally comprises one or more blue-dyeing compounds of different structure selected from the group consisting of disazo, copper formazan, triphendioxazine, and anthraquinone compounds.

* * * * *